United States Patent
Dale et al.

(10) Patent No.: US 10,907,189 B2
(45) Date of Patent: *Feb. 2, 2021

(54) METHODS AND DEVICES TO DETECT STROKE IN A SUBJECT

(71) Applicant: Sarissa Biomedical Limited, Coventry (GB)

(72) Inventors: Nicholas Dale, Coventry (GB); Chris Imray, Coventry (GB); Faming Tian, Coventry (GB)

(73) Assignee: SARISSA BIOMEDICAL LIMITED, West Midlands (GB)

( * ) Notice: Subject to any disclaimer, the term of this patent is extended or adjusted under 35 U.S.C. 154(b) by 194 days.

This patent is subject to a terminal disclaimer.

(21) Appl. No.: 15/580,575

(22) PCT Filed: Jun. 3, 2016

(86) PCT No.: PCT/GB2016/051638
§ 371 (c)(1),
(2) Date: Dec. 7, 2017

(87) PCT Pub. No.: WO2016/198838
PCT Pub. Date: Dec. 15, 2016

(65) Prior Publication Data
US 2018/0163245 A1    Jun. 14, 2018

(30) Foreign Application Priority Data

Jun. 9, 2015 (GB) .................................. 1509973.2

(51) Int. Cl.
*G01N 27/327*    (2006.01)
*C12Q 1/00*    (2006.01)
(Continued)

(52) U.S. Cl.
CPC ............ *C12Q 1/005* (2013.01); *C12Q 1/004* (2013.01); *G01N 27/3271* (2013.01);
(Continued)

(58) Field of Classification Search
CPC ............ G01N 27/327–27/3272; C12Q 1/004
See application file for complete search history.

(56) References Cited

U.S. PATENT DOCUMENTS 8,417,314 B2 * 4/2013 Dale .................... C12Q 1/004
204/403.04

FOREIGN PATENT DOCUMENTS

| WO | 2008081193 | 10/2008 |
| WO | 2009020860 | 2/2009 |
| WO | 2014087137 | 6/2014 |

OTHER PUBLICATIONS

PCT Search Report prepared for PCT/GB2016/051638, dated Sep. 13, 2016.

(Continued)

*Primary Examiner* — Alexander S Noguerola
(74) *Attorney, Agent, or Firm* — Brannon Sowers & Cracraft PC

(57) ABSTRACT

The invention describes a method of determining the presence of acute cerebral ischaemic disorder in a subject comprising: a. measuring the concentration of one or more purines in a body fluid of the subject, the purines being selected from adenosine, inosine, hypoxanthine, xanthine and ATP, and b. comparing the measured concentration with a threshold concentration of the one or more purines, wherein the threshold concentration is preferably in the range 5 μM to 15 μM and wherein a measured concentration higher than the threshold concentration indicates the presence of acute ischaemic disorder. Also is described a method of determining the absence of an acute cerebral disorder in a subject comprising: a. measuring the concentration of one (Continued)

or more purines in a body fluid of the subject, the purines being selected from adenosine, inosine, hypoxanthine, xanthine and ATP, and b. comparing the measured concentration with a threshold concentration of the one or more purines, wherein the threshold concentration is preferably below 4 $\mu M$ and wherein a measured concentration lower than the threshold concentration indicates the absence of acute cerebral ischaemic disorder.

22 Claims, 7 Drawing Sheets

(51) Int. Cl.
  G01N 33/53  (2006.01)
  G01N 33/543  (2006.01)
(52) U.S. Cl.
  CPC ..... *G01N 33/5308* (2013.01); *G01N 33/5438* (2013.01); *G01N 2800/2871* (2013.01); *G01N 2800/7019* (2013.01)

(56) References Cited

OTHER PUBLICATIONS

Bøhmer, T., J. Kjekshus, and P. Vaagenes. "Biochemical indices of cerebral ischemic injury." Scandinavian journal of clinical and laboratory investigation 43.3 (1983): 261-265.

Dale, Nicholas, and Bruno G. Frenguelli. "Measurement of purine release with microelectrode biosensors." Purinergic signalling 8.1 (2012): 27-40.

Weigand, Markus A., et al. "Adenosine A Sensitive Indicator of Cerebral Ischemia during Carotid Endarterectomy." Anesthesiology: The Journal of the American Society of Anesthesiologists 91.2 (1999): 414-421.

Pasini, Franco Laghi, et al. "Increase in plasma adenosine during brain ischemia in man: a study during transient ischemic attacks, and stroke." Brain research bulletin 51.4 (2000): 327-330.

Berne, Robert M., Rafael Rubio, and Richard R. Curnish. "Release of adenosine from ischemic brain." Circulation Research 35.2 (1974): 262-271.

Van Wylen, D. G. "Effect of ischemic preconditioning on interstitial purine metabolite and lactate accumulation during myocardial ischemia." Circulation 89.5 (1994): 2283-2289.

Matherne, G. Paul, et al. "Interstitial transudate purines in normoxic and hypoxic immature and mature rabbit hearts." Pediatric research 28.4 (1990): 348-353.

Swanström, Sten, and Lars-Eric Bratteby. "Hypoxanthine as a test of perinatal hypoxia as compared to lactate, base deficit, and pH." Pediatric research 16.2 (1982): 156-160.

PCT Search Report prepared for PCT/GB/2016/051641, dated Sep. 9, 2016.

Farthing, Don E., Christine A. Farthing, and Lei Xi. "Inosine and hypoxanthine as novel biomarkers for cardiac ischemia: From bench to point-of-care." Experimental Biology and Medicine 240.6 (2015): 821-831.

Mei, David A., Garrett J. Gross, and Kasem Nithipatikom. "Simultaneous determination of adenosine, inosine, hypoxanthine, xanthine, and uric acid in microdialysis samples using microbore column high-performance liquid chromatography with a diode array detector." Analytical biochemistry 238.1 (1996): 34-39.

Martin, C., Leone, M., Viviand, X., Ayem, M. L., & Guieu, R. (2000). High adenosine plasma concentration as a prognostic index for outcome in patients with septic shock. Critical care medicine, 28(9), 3198-3202.

Rai, A. K., Thakur, C. P., Velpandian, T., Sharma, S. K., Ghosh, B., & Mitra, D. K. (2011). High concentration of adenosine in human visceral leishmaniasis despite increased ADA and decreased CD73. Parasite immunology, 33(11), 632-636.

Issel, E. P., Lun, A., Pohle, R., & Gross, J. (1982). Hypoxanthine levels in amniotic fluid: An indicator of fetal hypoxia?. Journal of Perinatal Medicine—Official Journal of the WAPM, 10(5), 221-225.

Tian, Faming, Enrique Llaudet, and Nicholas Dale. "Ruthenium purple-mediated microelectrode biosensors based on sol-gel film." Analytical chemistry 79.17 (2007): 6760-6766.

Hong, Zhang. "1,\Murong Shengxing 1,\Liu Youyao 2, et al (1. Department of Neurology, 1st Affiliated Hospital,\2. Department of Biochemistry, Fujian Medical University, Fuzhou, 350005); Changes of NO and cGMP in Different Brain Regions at Early Stage during Cerebral Ischemia in Rats [J]." Journal of Fujian Medical University 3 (1998).

Galvani, Marcello, Donatella Ferrini, and Filippo Ottani. "Natriuretic peptides for risk stratification of patients with acute coronary syndromes." European journal of heart failure 6.3 (2004): 327-333.

"Expression difference between high-sensitivity C-reactive protein (hs-CRP) and N-terminal pro-brain natriuretic peptide (NT-proBNP) precursors in acute coronary syndromes (ACS) of different degrees" China Academic Journal Electronc Publishing House, May 14, 2013; 2540-2541; (English Translation of Abstract).

* cited by examiner

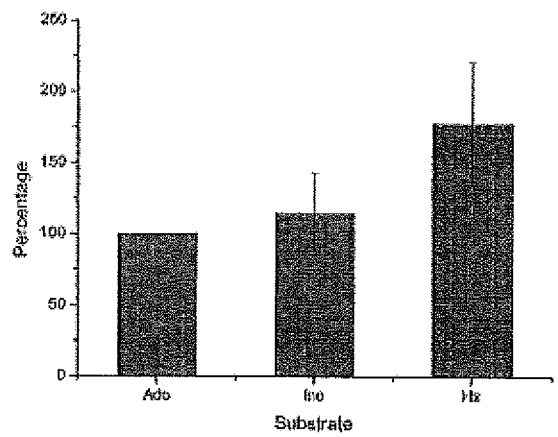
Figure 6a
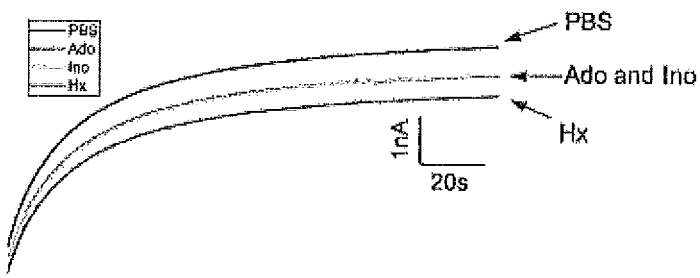
Figure 6b
| eqvt [Ado] | [Ado] | [Ino] | [Hx] |
|---|---|---|---|
| 2.15 | 1 | 1 | |
| 2.95 | | 1 | 1 |
| 2.8 | 1 | | 1 |
| 3.95 | 1 | 1 | 1 |
| 2 | 2 | | |
| 2.3 | | 2 | |
| 3.6 | | | 2 |
| 4.3 | 2 | 2 | |
| 5.6 | 2 | | 2 |
| 5.9 | | 2 | 2 |
| 7.9 | 2 | 2 | 2 |
Figure 6c

METHODS AND DEVICES TO DETECT STROKE IN A SUBJECT

CROSS-REFERENCE TO RELATED APPLICATION

This application is a U.S. national entry application under 37 C.F.R. § 371(b) of International Application Serial No. PCT/GB2016/051638 filed on Jun. 3, 2016, which claims the right of priority and benefit under 35 U.S.C. §§ 119 & 365 of GB Patent Application No. 1509973.2 filed on Jun. 9, 2015, the disclosures of which are incorporated herein by reference in their entirety. This application also cross-references co-pending International Application Serial No. PCT/GB2016/051641 filed on Jun. 3, 2016, which claims the right of priority and benefit under 35 U.S.C. §§ 119 & 365 of GB Patent Application No. 1509974.0 filed on Jun. 9, 2015, the disclosures of which are incorporated herein by reference in their entirety.

FIELD

The present invention relates to apparatus and methods to measure a physiological condition of a subject, and in particular to detect the presence or absence of acute ischaemic disorder such as stroke in a subject such as a human patient.

BACKGROUND

Ischaemia is a restriction in blood supply to tissues which results in a shortage of oxygen and glucose needed for cellular metabolism. Typically ischemia results from occlusion or rupture of blood vessels, with resultant damage to or dysfunction of tissue. Acute ischaemic disorder, such as ischaemic stroke, haemorrhagic stroke, transient ischaemic attack (TIA), and cardiovascular disease such as myocardial infarction (MI) may have a sudden and unpredicted onset and rapid diagnosis and treatment is needed. Stroke and MI may be diagnosed through overt symptoms, but in some circumstances detection of acute ischaemic disorder may be confounded by other conditions of the patient, such as unconsciousness or inebriation, and in stroke there is a need to ascertain that the stroke is ischaemic or haemorrhagic, in order to administer clot-dissolving drugs quickly. In 85% of cases stroke is not diagnosable from a CT scan shortly after occurrence, and only becomes apparent at later times, such as up to 24 hr after the event, whereas treatment needs to be started rapidly in order to be effective. There is a strong need for improved, rapid means of detecting acute, severe ischaemia in a subject in order to inform diagnosis and treatment of acute ischaemic disorder.

Cellular metabolism is driven by the disequilibrium between ATP and ADP (Nicholls D G, Ferguson S J. Bioenergetics 2. London: Academic Press; 1992) (all references cited herein are incorporated by reference), and so enzymatic pathways exist in cells to rapidly remove ADP and in effect convert it to adenosine (Sims R E, Dale N. Activity-Dependent Adenosine Release May Be Linked to Activation of Na(+)-K(+) ATPase: An In Vitro Rat Study. PLoS One 2014; 9(1)) and the downstream purines inosine and hypoxanthine. In ischaemic disease, tissue hypoxia results in the loss of the ability of cells to make ATP and results in the intracellular accumulation of adenosine and downstream purines, which can then efflux via equilibrative transporters. Although a few studies have examined whether purine levels in blood increase during acute events such as stroke (Laghi Pasini F et al. Increase in plasma adenosine during brain ischemia in man: a study during transient ischemic attacks, and stroke. *Brain Res Bull* 2000; 51(4): 327-30) and brain ischaemia during carotid endarchectomy procedures (Weigand M A, et al. Adenosine: a sensitive indicator of cerebral ischemia during carotid endarterectomy. *Anesthesiology* 1999; 91(2): 414-21), this has not been widely studied.

While it is known from the prior art that levels of purines are elevated in conditions of acute local hypoxia/ischaemia, there has been no effective establishment in the prior art of a method to determine with confidence the presence of acute ischaemia, which may inform diagnosis and treatment. These previous studies have relied on measurements made in clinical analysers remote from the subject and, owing to the rapid breakdown of purines by enzymes in whole blood, samples need to be frozen immediately after being taken, transported frozen to the instrument, thawed and then separated into plasma; thawing and separation are slow processes, which leads to significant breakdown of purines in the sample. This sequence of events leads to insensitive and unreliable measurements and is not suited to routine clinical practice. It is an object of the present invention to provide methods and devices to allow measurement of purines to be related to the presence of acute ischaemia in a subject such as a human patient, and in some embodiments to the presence of an acute ischaemic disorder such as stroke in the subject.

DESCRIPTION OF THE INVENTION

According to a first aspect, the invention provides a method of determining the presence of acute ischaemic disorder, such as an acute cerebral ischaemic disorder, in a subject comprising:
  measuring the concentration of one or more purines in a body fluid of the subject, the purines being selected from adenosine, inosine, hypoxanthine, xanthine and ATP, and comparing the measured concentration with a threshold concentration of the one or more purines,
wherein the threshold concentration is typically in the range around 5 µM to around 15 µM and wherein a measured concentration higher than the threshold concentration indicates the presence of acute ischaemic disorder.

The acute cerebral ischaemic disorder may be a stroke such as ischaemic stoke or haemorrhagic stroke or caused by a traumatic head injury or a transient ischaemic attack (TIA).

The invention also provides measuring purines in the same manner where a measurement below a threshold of 4 µM or below 3 µM or below 2 µM indicates that the subject does not have an acute cerebral ischaemic disorder, such as stroke or from a head injury. This can be used, for example, to distinguish such disorders from symptoms that mimic stroke, such a Bell's palsy, Todd's paresis or migraines. This improves the identification of treatment for the patient and may reduce the need for a patient to be treated in a specialist stroke care department at a hospital.

In some embodiments the measured concentration may be used to indicate a probability that acute ischaemic disorder is present in the subject or a degree of risk that the acute ischaemic disorder may progress and become more serious, a lower measured concentration indicating a lower probability or degree of risk and a higher concentration indicating a higher probability or degree of risk.

In some embodiments the acute ischaemic disorder is a stroke and the method comprises comparing the measured concentration with a threshold concentration characteristic of a stroke and determining that a stroke has occurred if the measured concentration is above the threshold concentration.

In this way the invention provides a method of determining that covert acute ischaemic disorder is present in the subject, in which the presence of acute ischaemic disorder or a medical condition causing or resulting from it is not apparent from a physical examination of the subject.

Typically a subject may present with one or more classical symptoms of stroke, such as slurred speech, unilateral weakness or paralysis, one sided facial paralysis or unconsciousness, and the method is used together with a diagnosis based on the symptom(s) to determine that the subject has had a stroke.

Typically the method of the invention is used together with a cranial scan such as a CT or MRI scan to determine that the subject has had a stroke. The method and the cranial scan may be used together to provide improved information to a clinician compared with the information from the method or a cranial scan alone. The results of the method and the cranial scan may be used together to determine if a patient has an ischaemic or a heamorrhagic stroke.

In this way the invention provides a method of diagnosing stroke in a subject, in some embodiments a method of diagnosing an ischaemic stroke, and in some embodiments a method of diagnosing a heamorrhagic stroke.

The method may comprise administering a procedure to the patient, such as administering a clot-dissolving drug to a subject diagnosed with an ischaemic stroke. A clot-dissolving drug may be as known in the art, such as a tissue plasminogen activator (TPA).

In some embodiments the threshold concentration is in the range 5 µM to 10 µM, in some embodiments in the range 8 µM to 12 µM, in some embodiments in the range 10 µM to 14 µM, and in some embodiments in the range 10 µM to 15 µM.

In some embodiments the method comprises comparing a measured concentration with the threshold concentration and using the difference between the measured concentration and the threshold concentration to determine a probability that a subject has suffered a stroke or a risk that the subject may later suffer a further stroke. For example, a measured concentration far above the threshold may indicate a higher said probability or risk and a measured concentration close to the threshold may indicate a lower probability or risk.

In some embodiments the measured concentration or the difference between a measured concentration and the threshold concentration may be used to determine the severity of an acute ischaemic condition such as stroke, a higher measured concentration or greater difference indicating greater severity.

Accordingly, in some embodiments the invention provides a method of prognosis for an acute ischaemic condition. A higher measured concentration or greater difference may indicate a poorer prognosis. The method may comprise allocating a subject to receive a treatment based on the prognosis.

A subject may be a post partum human subject, such as child of age over 3 months, 6 months, 1 year, 5 years or 10 years, or an adult of age 15 years or more.

A subject may be a neonate, or a baby in utero. The method may comprise measuring the purine concentration in a body fluid of a baby at one or more occasions before, during or after birth in order to determine a acute ischaemic condition of the baby.

In this way the method provides a means of prioritising a subject for treatment or for further investigation, such as prioritising the subject for a cranial scan, a purine concentration greater than the threshold indicating a higher priority, and a concentration below the threshold indicates a lower priority or no need for further action. The method further provides a means of allocating a subject to a subpopulation of subjects, a purine concentration greater than the threshold being used to allocate the subject to a first subpopulation, such as a subpopulation having a more serious ischaemic condition or being at greater risk of harm from such a condition, and a concentration below the threshold being used to allocate the subject to a second subpopulation.

The threshold concentration may be selected to provide suitable discrimination between higher and lower probability that an acute ischaemic condition is present for a patient population as a whole, or selected to provide such discrimination for a subpopulation. In some embodiments the method comprises allocating a subject to a subpopulation and then selecting a further threshold concentration for use in the method that is suitable for the said subpopulation. For example, the subpopulation may comprise subjects having a specific medical condition or suspected medical condition, such as a suspected TIA or having a history of TIAs, and may be characterised by other subject-specific factors such as age, weight, sex or smoking/non-smoking.

A threshold concentration may be selected for use in the method according to the embodiment. A threshold concentration may be selected in the range 5 to 15 µM, 8 to 12 µM or 10 to 15 µM, such as 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0 µM. The threshold concentration may be selected according to a subpopulation of subjects with whom the method is to be used. The threshold concentration may be selected to give an appropriate selectivity and specificity to the method, in determining the presence of acute ischaemic disorder in a subject. In some embodiments the method comprises modifying the threshold concentration in the light of observation of outcomes resulting from such determination.

Herein for clarity and brevity a concentration being greater than a threshold concentration is taken to include that the concentration is equal to the threshold concentration. In some embodiments a concentration being lower than a threshold concentration includes that the concentration is equal to the threshold concentration.

According to the embodiment, a body fluid may be whole blood, serum, plasma or cerebrospinal fluid. Typically a body fluid is whole blood, serum or plasma. Blood, serum or plasma may be arterial blood, venous blood and may be peripheral blood. The body fluid may be diluted or mixed with a further liquid or compound before a measurement is made.

In various embodiments, the measured concentration and the threshold concentration may be (i) those of a single purine selected from the said purines, measured individually;

(ii) a total of the concentrations of two or more said purines, each measured individually;

(iii) a weighted sum of the concentration of two or more said purines, each measured individually, for example of the form:

$$\text{total concentration} = A \times [\text{purine}(1)] + B \times [\text{purine}(2)],$$
where square brackets denote concentration;

(iv) an equivalent total purine concentration measured by a measurement method responsive to two or more said purines, the total purine measurement being calibrated relative to the response of the method to a single purine;

(v) a weighted sum of two or more said measurements of total purines, for example of the form total concentration=$A$×[purine(1) and purine(2)]+$B$×[purine(3) and purine(4)].

In methods (iv) and (v) the response of the measurement method may be such that the response to a second purine is a known function, such as a ratio, of the response to the first, such that when calibrated with a known concentration of the first purine, the response to the second purine is known.

In some embodiments the measured and threshold concentrations are total purine concentrations derived from a measurement method sensitive to three, four or five of the said purines, wherein the measurement is calibrated relative to the response to a calibration purine, the measurement method having a known ratio of the response to the calibration purine to the response to each of the remaining purines.

For example the said three purines may be adenosine, inosine and hypoxanthine and the calibration purine may be one of the three purines, typically adenosine. The said four purines may be adenosine, inosine, hypoxanthine and xanthine and the calibration purine may be one of the four purines, typically adenosine.

In such methods the ratio of responses of the measurement method, or a measurement device such as a sensor, to hypoxanthine, xanthine and inosine to that of adenosine may be known from the parameters of the method or device, and the method may comprise comparing the response to all the purines present in the sample with the response to a known concentration of adenosine to derive a value of total purine concentration in terms of an equivalent concentration of adenosine.

For example, a measurement device such as a sensor may have a response S given by:

$S=A$[adenosine]+$B$[inosine]+$C$[hypoxanthine]+$D$[xanthine]

where the values of the calibration factors A, B, C and D are substantially constant with concentration, such that the ratios of the responses to each of inosine, hypoxanthine and xanthine to that of adenosine are constant values $b=B/A$, $c=C/A$ and $d=D/A$.

The measurement response $S_m$ to a combination of purines in a sample is:

$S_m=A$([adenosine]$_m$+$b$·[inosine]$_m$+$c$·[hypoxanthine]$_m$+$d$·[xanthine]$_m$)

The calibration response to a known concentration of adenosine [adenosine]$_{cal}$ is:

$S_c=A$[adenosine]$_{cal}$ $S_m$ may be expressed in terms of an equivalent concentration of adenosine, [adenosine]':

$S_m=S_c$([adenosine]'/[adenosine]$_{cal}$), where [adenosine]'=[adenosine]$_m$+$b$·[inosine]$_m$+$c$·[hypoxanthine]$_m$+$d$·[xanthine]$_m$ Accordingly, in some embodiments the measured concentration of total purines may be the equivalent concentration of adenosine, [adenosine]'.

For a measurement method which is equally sensitive to each purine, the factors b, c and d are all equal to 1 and [adenosine]' is simply the sum of the individual purine concentrations. Certain enzyme sensors comprising a cascade of enzymes to react each of the purines to a common measurand such as hydrogen peroxide may fall into this category, as will be discussed below. In general, a sensor may have different sensitivities to each purine, the factors b, c, and d being known from the inherent properties of the sensor or found by calibration during manufacturing.

Accordingly, in some embodiments the measured concentration of the said one or more purines is expressed in terms of an equivalent concentration of one purine, the response of the sensor being calibrated using the said purine, and the threshold concentration is a value of the said equivalent concentration.

Accordingly, in some embodiments the method comprises:

(i) measuring the measurement response of a measurement device responsive to more than one purine selected from adenosine, inosine, hypoxanthine, xanthine and ATP when contacted with a sample comprising a body fluid, (ii) measuring the calibration response of the measurement device to a calibration concentration of one of the said purines, (iii) deriving the equivalent concentration of the said one purine that would result in the same measurement response when present alone of the said purines in the sample, and (iv) comparing the said equivalent concentration with a threshold value of the equivalent concentration, wherein the threshold concentration is typically in the range 5 µM to 15 µM and wherein a measured equivalent concentration higher than the threshold concentration indicates the presence of acute ischaemic disorder.

The measurement device may be a biosensor as described herein.

The measured concentration may be derived in terms of a value of concentration, or may be derived as a measured signal from the measurement device, the measured signal being calibrated in comparison with a calibration signal measured when a known concentration of a purine is present, the threshold concentration being expressed as a threshold value of the signal.

In some embodiments the method comprises:

(i) measuring a measurement signal from a measurement device when contacted with a plurality of purines in a sample of a body fluid from a subject, (ii) measuring a calibration signal when contacted with a calibration purine, (iii) using the measurement signal and the calibration signal to derive an equivalent signal representative of the equivalent concentration of the calibration purine, and (iv) comparing the equivalent signal with a threshold signal value representing a threshold equivalent concentration, wherein an equivalent signal greater than the threshold signal value indicates the presence of ischaemia in the subject.

In some embodiments the method comprises measuring the concentration of one or more purines independently of other purines, and comparing the measured concentration with a threshold concentration for the said purine. The purine may be one of adenosine, xanthine, inosine or ATP and the threshold concentration may be in the range 5 µM to 10 µM. The purine may be hypoxanthine and the threshold concentration may be in the range 5 µM to 15 µM.

The purines may be adenosine, inosine, hypoxanthine and xanthine, the calibration purine may be adenosine, and the threshold concentration may be in the range 5 µM to 15 µM.

The purines may be inosine, hypoxanthine and xanthine, the calibration purine may be inosine, and the threshold concentration may be in the range 5 µM to 15 µM.

The purines may be hypoxanthine and xanthine, the calibration purine may be hypoxanthine, and the threshold concentration may be in the range 5 µM to 15 µM.

In this way in some embodiments the actual concentration of each individual purine is not derived, and the measured concentration of the one or more purines is not necessarily a summation of the individual concentrations of the purines present in the sample; rather the measured concentration may be a value indicative of the total purine content of the sample, which is then compared with a threshold value to determine the presence of acute ischaemic disorder in the patient.

A change in the concentration of a purine in a body fluid of a subject may indicate covert acute ischaemic disorder and may indicate progression or resolution of an acute ischaemic disorder.

In some embodiments the method comprises:
measuring the concentration of one or more of the said purines at each of a first and a second time points,
comparing the change in measured concentration with a threshold value for the change and
determining that acute ischaemic disorder is present in the subject if the change is above the threshold value.

The threshold value of the change may be in the ranges 1 µM to 8 µM between the first and the second measurement, or 2 µM to 4 µM, or 1 µM to 3 µM, or above 8 µM between the first and the second measurement. The first and second measurement may be separated by a time interval in the range 5 minutes to 48 hours, such as 5 to 30 minutes, 15 minutes to 2 hours, 30 minutes to 8 hours, 1 hour to 24 hours, 2 hours to 48 hours. In this way a first measurement may be made to determine the presence of, or the probability of the presence of, an acute ischaemic disorder, and a second measurement may be made at the said time interval after the first. A rise in the measured concentration may be used to determine the presence of acute ischaemic disorder such as stroke, the progression of the disorder, such as spread in the area of ischaemic damage following a stroke. A fall in the measured concentration may be used to determine resolution of the disorder, for example following use of a clot-dissolving drug to restore perfusion.

The change may be a change in the measured concentration of a single purine, or of the measured total concentration as described herein of two or more purines.

In some embodiments the method comprises:
a. measuring the concentration of one or more said purines at each of a first and a second time points,
b. using a measured concentration at one time point together with the change in a measured concentration between the first and the second time points to determine the presence of acute ischaemic disorder in the subject.

The presence of acute ischaemic disorder may be indicated by the combination of (i) a concentration of one or more purines being above a threshold concentration and (ii) a change in the measured concentration of one or more purines being above a threshold value for the change.

The method may comprise deriving a value indicative of the probability that acute ischaemic disorder is present in a subject or risk of the subject later suffering a further acute ischaemic disorder. For example a value V may be derived from an equation of form:

$$V = A \cdot [\text{purines}] + B \cdot (\text{change in [purines]}),$$

where A and B are constant or a function of further variables, such as a function of other risk factors for acute ischaemic disorder specific for an individual or subpopulation of which the individual is a member.

In some embodiments the presence of acute ischaemic disorder may be indicated by the combination of (i) a concentration of one or more purines above a threshold concentration and (ii) a rate of change of one or more purines above a threshold value of the rate of change. The threshold rate of change may be in the ranges 0.05 µM/minute (min) to 1 µM/min, or 0.05 µM/min to 0.1 µM/min, 0.1 µM/min to 0.5 µM/min, or above 0.5 µM/min.

A value V as above may depend on the difference between the measured concentration or rate of change of concentration and the respective threshold values:

$$V = A \cdot ([\text{purines}] - \text{threshold concentration}) + B \cdot (\text{rate of change of [purines]} - \text{rate of change threshold})$$

In this way the presence of acute ischaemic disorder may be indicated with more confidence than for measurement of a concentration at a single time, which may arise from a confounding effect, by observing a trend leading towards a higher concentration. In some embodiments a lower threshold for the concentration measurement, which on its own might result in a false positive result, may be used together with a change between a first and a second measurement being above a threshold to determine the presence of acute ischaemic disorder. For example, in such embodiments a concentration threshold may be in the range 5 µM to 10 µM, and the change threshold may be in the range 1 µM to 8 µM between a first and second measurement. Similarly a fall in measured concentration between a first and second measurement may indicate resolution of the disorder.

In some embodiments the concentration is measured by a biosensor responsive to the said one or more purines. The biosensor may be an enzyme sensor, comprising one or more enzymes for which one of the said purines is a substrate. The biosensor may be sensitive to two or more said purines, such that the biosensor provides a signal representative of the total concentration of the two or more purines.

A concentration of a first purine may be measured as the difference between the signal from a biosensor responsive to both a first and a second purine and that from a biosensor responsive to the second purine alone.

A concentration as described herein may be represented by a signal from a biosensor sensitive to one or more purines, and a measurement of a concentration may comprise measuring the said signal and comparing the signal to a calibration value relating the signal to a known concentration of the said one or more purines.

Comparison of a measured concentration of one or more purines with a threshold concentration may be done by comparing a signal from a biosensor sensitive to the said one or more purines with a value of the said signal representative of the threshold concentration.

The concentration may be measured using a biosensor comprising an enzyme electrode comprising one or more immobilised enzymes, as described for example in U.S. Pat. No. 8,417,314 and EP1565565. Examples of suitable enzyme electrodes include:

(1) ATP may be measured with an enzyme electrode biosensor comprising glycerol kinase and glycerol-3-phosphate oxidase, wherein the glycerol kinase and glycerol-1,3-phosphate oxidase catalyse a reaction of ATP in the sample to form glycerine phosphate and hydrogen peroxide ($H_2O_2$) and the electrode detects the $H_2O_2$ produced in the reaction.

(2) The combined concentration of hypoxanthine and xanthine may be measured with an enzyme electrode biosensor comprising xanthine oxidase, wherein the xanthine oxidase catalyses a reaction of the hypoxanthine to form urate and $H_2O_2$ and the electrode detects the $H_2O_2$ produced in the reaction.

(3) The combined concentration of inosine, hypoxanthine and xanthine may be measured with an enzyme electrode biosensor comprising nucleoside phosphorylase and xanthine oxidase, wherein the nucleoside phosphorylase catalyses a reaction of inosine to form hypoxanthine and the xanthine oxidase catalyses a reaction of the hypoxanthine to form urate and $H_2O_2$ and the electrode detects the $H_2O_2$ produced in the reaction.

(4) The combined concentration of adenosine, inosine, hypoxanthine and xanthine may be measured with an enzyme electrode biosensor comprising adenosine deaminase, nucleoside phosphorylase and xanthine oxidase, wherein the adenosine deaminase catalyses a reaction of adenosine to form inosine, the nucleoside phosphorylase catalyses a reaction of inosine to form hypoxanthine and the xanthine oxidase catalyses a reaction of the hypoxanthine to form urate and $H_2O_2$ and the electrode detects the $H_2O_2$ produced in the reaction.

A concentration of a single purine may be derived form the difference between measurements of the combined concentration of more than one purine as measured by such biosensors as (1) to (4). For example a concentration of adenosine may be derived from the difference between a measurement made by the enzyme electrode (4) above sensitive to adenosine, inosine, hypoxanthine and xanthine and a measurement made by the enzyme electrode (3) above sensitive to inosine, hypoxanthine and xanthine.

The signal from the biosensor may be a value of a current flowing through the electrode, and a measurement may be represented by a current. A threshold concentration may be represented by a threshold current and comparison of a measured concentration with a threshold concentration may be achieved by comparison of the respective currents.

The biosensor signals, such as in the form of a current from the biosensor, may be corrected for interferences not related to purine content by subtraction of a control signal such as a current from a 'null' biosensor as described below, without enzymes in the sensing layer, in contact with the same sample, reference or calibration liquid.

Calibration of a sensor may be done by contacting the sensor with a liquid containing a known concentration of a purine. A purine may be added to a sample to 'spike' the sample to allow calibration. In some embodiments a sensor is sensitive to more than one purine and calibration is done by contacting the sensor with one of the said purines, the response of the sensor to the total concentration of the said purines being derived from the response to the single said calibration purine. For example a biosensor comprising an enzyme electrode (4) as described above that is sensitive to adenosine, inosine, hypoxanthine and xanthine may be calibrated by contacting the sensor with a known concentration of adenosine, the response to the adenosine being used to calibrate the response of the sensor to the remaining purines. In enzyme sensors of this type typically the calibration uses the purine which passes through the entire enzymatic reaction cascade. In this way correct functioning of the enzyme cascade and response to purines that enter further down the reaction cascade are ascertained.

The biosensor may be configured to be equally sensitive to each of the purines that it senses. For example, an enzyme sensor (4) as described above may be configured such that substantially all of the inosine produced in the reaction of adenosine catalysed by adenosine deaminase is reacted by the enzyme cascade to form $H_2O_2$. In this way the sensor may have a substantially equal response to inosine as to adenosine. The same may apply to the reactions of inosine, hypoxanthine and xanthine, such that the sensor is substantially equally responsive to each of the purines. In this way the sensor is configured to measure the total concentration of purines substantially equal to the sum of their individual concentrations.

In some embodiments the relationship between the sensitivities of the sensor to different purines may be known, and may for example be a property of the design of the sensor, such that the sensitivity to a second purine will lie within a range of the sensitivity to the first. In this way the response to a second purine may be derived from the response to a first. For example, the response to inosine, hypoxanthine or xanthine may be a known percentage of the response to adenosine, or may lie within a known range of percentages of the response to adenosine. In some embodiments the response to 'total purines' is the response to all the purines present in the sample, calibrated by the response to a single purine, and the response to an individual purine is not derived.

In some embodiments the body fluid is whole blood, for example peripheral whole blood. Biosensors of the kind referred to in U.S. Pat. No. 8,417,314 and EP1565565, comprising a ruthenium purple mediator, and as exemplified below are suited to rapid measurements in whole blood.

Accordingly, the method may comprise measuring a concentration of one or more purines using a biosensor comprising an electrode having immobilised on it an enzyme for which the said purine is a substrate and a ruthenium purple mediator.

In some embodiments the method comprises:
  contacting a biosensor adapted to measure the concentration of one or more purines selected from adenosine, hypoxanthine, xanthine, inosine and ATP, with a reference liquid such as a buffer,
  measuring a reference signal at a first elapsed time after the biosensor is contacted with the reference liquid,
  contacting the biosensor with a body fluid,
  measuring a measurement signal at a second elapsed time after the biosensor is contacted with the body fluid, and
  deriving a measurement of the concentration of one or more purines from the measurement and reference signals.

An elapsed time may be selected to be within the range 5 seconds (s) to 600 s, in the range 10 s to 300 s, or in the range 30 s to 180 s, such as 90, 120, 150 or 180 s.

Typically the first and the second elapsed times are substantially the same, such as within 10%, 5% or 2% of each other.

In some embodiments the method comprises:
  contacting the biosensor with a liquid comprising a known concentration of a purine measuring the calibration signal at a third elapsed time after the biosensor is contacted with said liquid, and
  comparing the measurement signal with the calibration signal to derive a measurement of concentration of one or more purines.

Typically the first, second and third elapsed times are substantially the same, such as within 10%, 5% or 2% of each other.

In some embodiments the method comprises:
  subtracting the reference signal from the measurement signal to derive a corrected measurement signal, subtracting the reference signal from the calibration signal to derive a corrected calibration signal, and deriving the concentration measurement from the ratio of the corrected measurement signal to the corrected calibration signal.

The calibration liquid may be a buffer comprising a known concentration of a purine or may be a sample from a subject comprising a known concentration of a purine added into the sample.

The method may comprise taking a sample of the body fluid and measuring the amount or concentration of one or more purines in the sample. In some embodiments the sample may be taken by means known in the art, for example using a Vacutainer™ and may be tested immediately without prior treatment of the sample.

In some embodiments the invention provides a method of monitoring the response of a subject to a clinical procedure such as surgery or drug therapy comprising measuring the concentration of one or more purines as described herein at one or more intervals after the procedure to determine the efficacy of the procedure in changing the measured concentrations. The method may be used to determine the need for further intervention, such as extended follow-up or a further procedure, or to determine a probability that the subject will need such further intervention. For example, a drop in the measured concentration of purines may indicate success in an intervention to relieve acute ischaemic disorder.

The clinical procedure may comprise administering a clot-dissolving drug as known in the art, such as a tissue plasminogen activator (TPA).

The method may comprise:
measuring a baseline concentration of one or more said purines,
carrying out the clinical procedure,
measuring a concentration of the said one or more purines at one or more intervals after the procedure
comparing a concentration with the baseline concentration, wherein a difference between the said concentrations is used to determine the a change in the degree of acute ischaemic disorder present in the subject.

The method may comprise:
measuring a baseline trend in concentration over time of one or more said purines, carrying out the clinical procedure,
measuring a concentration of the said one or more purines at one or more intervals after the procedure,
comparing a trend in concentration after the procedure with the baseline trend, wherein a difference between the said trends is used to determine the a change in the degree of acute ischaemic disorder present in the subject.

The measured concentration may be compared with a threshold value to determine the success or otherwise of the procedure.

A change in the degree of acute ischaemic disorder present in the subject may be used to determine for example one or more of a measure of success of the procedure, a probability that the subject will need further intervention and a risk that the subject may go on to develop an acute ischaemic medical condition.

According to a second aspect the invention provides a device configured to carry out a method as described herein. Typically the device comprises a biosensor adapted to measure the concentration of one or more purines in a body fluid, the purines being selected from adenosine, inosine, hypoxanthine, xanthine and ATP.

The biosensor may comprise an enzyme electrode having immobilised on it an enzyme for which one of the said purines is a substrate and a ruthenium purple mediator, for example an enzyme electrode responsive to all four of adenosine, inosine, hypoxanthine and xanthine, for example as disclosed in U.S. Pat. No. 8,417,314

In some embodiments the device is configured to carry out a method as described herein to determine the presence of acute ischaemic disorder in, or to measure a degree of acute ischaemic disorder present in, a subject.

In some embodiments the device further comprises a controller configured to measure signals from the biosensor and to:
measure a reference signal at a first elapsed time after the biosensor is contacted with a reference liquid,
measure a measurement signal at a second elapsed time after the biosensor is contacted with a body fluid, and
derive the measured concentration of the one or more purines from the said signals.

Typically the first and the second elapsed times are substantially the same.

In some embodiments the controller is configured to:
measure a calibration signal at a third elapsed time after the biosensor is contacted with said liquid, and
compare the measurement signal with the calibration signal to derive the measured concentration of the one or more purines.

Typically the first, second and third elapsed times are substantially the same.

In some embodiments the controller is configured to:
subtract the reference signal from the measurement signal to derive a corrected measurement signal,
subtract the reference signal from the calibration signal to derive a corrected calibration signal, and
derive the measured concentration of the one or more purines from the ratio of the corrected measurement signal and the corrected calibration signal.

In some embodiments the device comprises a liquid receiving element to receive and retain a body fluid from the subject and a biosensor in fluid communication with the liquid receiving element. The liquid receiving element may comprise a portion of a surface of a biosensor on which an enzyme electrode is provided. The liquid receiving element may comprise a test chamber and a biosensor may be provided within the test chamber. The device may comprise an inlet port to allow the reference liquid and the sample to be introduced into the test chamber. The device may be configured to receive a reference liquid and a sample introduced by a user, and to read a signal from the biosensor at a selected elapsed time after the liquid is introduced. The device may be configured to introduce a reference liquid into the test chamber and to introduce the sample into the test chamber under control of the controller. In some embodiments the device is configured to introduce a calibration liquid into the test chamber. The device may comprise one or more fluidic channels opening to the test chamber through which liquids such as the sample, reference and calibration liquids may be introduced. The device may comprise fluid actuation means such as a pump to cause the liquids to flow into the test chamber, and may comprise reservoirs for liquids each connected to the test chamber via a fluidic channel and optionally via a valve.

The device may comprise a controller to control the device and to implement the methods of the invention. The controller may control the flow of liquids and the measurement of purines and may compare measurements with threshold values as described herein. The device may report the purine measurements and may communicate data from the purine measurements, or from the comparison with threshold values to a remote receiving device such as a computer. The controller may be computer-implemented and may comprise a processor and instructions stored in a data store to control operation of the device.

The device may be configured to inter-fit with a sampling device, such as a Vacutainer™, as disclosed for example in pending international patent application WO2014087137. The device may be configured to take a sample from a subject, such as a blood sample, and to contact a biosensor forming part of the device with the sample as described herein.

Preferred features of the second aspect of the invention are as for the first aspect mutatis mutandis

BRIEF DESCRIPTION OF THE FIGURES

FIG. 6 shows the response of sensors as used in the example for inosine (Ino) and hypoxanthine (Hx) relative to the response to adenosine (Ado): (a) mean and SD of the response of 5 sensors normalised to the response of each sensor to adenosine; (b) response against time for one of the sensors in which response to inosine is close to that of adenosine and response to hypoxanthine is greater; (c) examples of combinations of micromolar concentrations of adenosine, inosine and hypoxanthine in a sample and the resulting measured 'total purine' concentration expressed as an equivalent micromolar concentration of adenosine, for sensors having the relative responses shown in (a).

DESCRIPTION OF AN EMBODIMENT OF THE INVENTION

Figure 1:
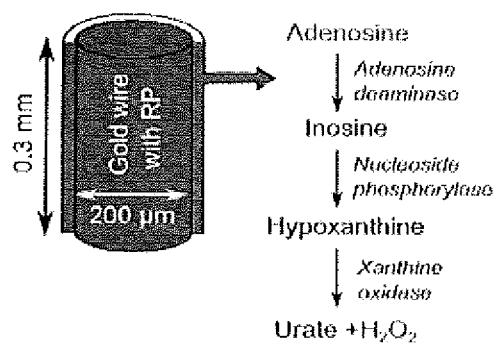
FIG. 1 shows a diagram of a sensing electrode forming part of an enzyme sensor usable to carry out the method, showing an enzymatic cascade used to detect the blood purines. The enzymes are entrapped within a layer on a Ruthenium Purple (RP) coated gold electrode.

In an embodiment the invention provides a method of determining the presence of acute ischaemic disorder in a subject comprising:

measuring the concentration of a plurality of purines in a body fluid of the subject, the purines being adenosine, inosine, hypoxanthine and xanthine, and comparing the measured concentration with a threshold concentration of the one or more purines, wherein the threshold concentration is in the range 5 µM to 15 µM and wherein a measured concentration greater than the threshold concentration indicates the presence of acute ischaemic disorder.

In this embodiment the method comprises measuring the concentration of adenosine, hypoxanthine, xanthine, and inosine using a biosensor responsive to all four said purines. The biosensor comprises (i) an enzyme electrode of type (4) as described previously and in U.S. Pat. No. 8,417,314 and (ii) a null sensor comprising an electrode identical to the enzyme electrode but without enzymes, to correct for background signals from liquid in contact with the biosensor, the signal from the biosensor at any give time being the difference between the enzyme electrode current and the null sensor current at that time. The enzyme electrode is calibrated with a single concentration of adenosine and the ratios of the response to the other three purines to that of adenosine are determined by the characteristics of the electrode, such as dimensions, physical and chemical properties of the enzyme layer and activity of the enzymes provided within them. The measured concentration is expressed as an equivalent concentration of adenosine as described previously, and is referred to below and in the example as a measurement of 'total purines'.

FIG. 6a shows the mean and SD of the response of five sensors of this kind as used in the example to inosine (ino) and hypoxanthine (hx) relative to the response of each sensor to adenosine (ado). From such data the response of the sensor can be related to the total purine content in the sample, allowing the overall response to be calibrated in terms of adenosine. For the example in FIG. 6a, the ratio b as described above for inosine response is around 1.15 and the ratio c for hypoxanthine response is around 1.80. Xanthine oxidase catalyses the reaction of hypoxanthine to form xanthine and $H_2O_2$, and then the reaction of xanthine to form urate and further $H_2O_2$, the electrode detecting the $H_2O_2$ produced in the reaction, so for electrodes of this kind the response to hypoxanthine will be close to twice that to xanthine. Ratio d will therefore be around 0.9.

FIG. 6b shows the response against time for a sensor in which response to inosine is close to that of adenosine and response to hypoxanthine is greater. It can be seen that the time courses of response to each purine overlie each other, allowing the relative responses at any time point to be determined simply as the difference between the trace in the presence of purine and the trace in PBS, and the response to that purine at any time point to be calibrated by the response to adenosine at the same time point.

In this way the 'total purine' response as described herein may be related to either known individual concentrations of the said purines, or a total known concentration of all of the said purines, present in the sample, to provide a measurement of the 'total purine concentration', in terms of an equivalent concentration adenosine, calibrated by a response to single purine such as adenosine.

FIG. 6c gives examples of the combinations of micromolar concentrations of adenosine, inosine and hypoxanthine that may be present within the sample and the resulting measured 'total purine' concentration, expressed as an equivalent micromolar concentration of adenosine, for sensors having the relative responses shown in FIG. 6a. It can be seen that for a range of combination of the concentrations of individual purines, the measured total purine concentration may lie in the range around 5 µM to around 15 µM.

It will be seen in the example below that comparison of the total purine concentration measured and calibrated in this way, with a threshold for the total purine concentration, where the threshold lies in the range 5 µM to 15 µM, is effective to indicate the presence of acute ischaemic disorder in a subject, and that measurement of individual purine concentrations is not required.

Figure 3:
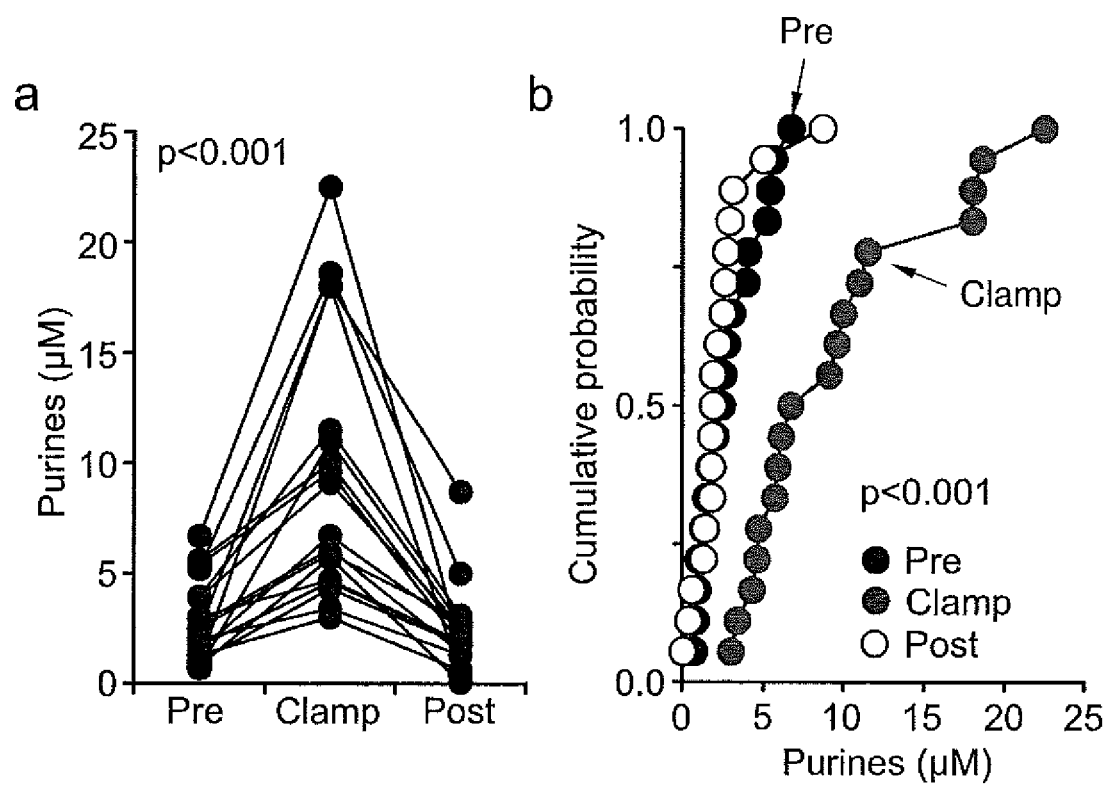
FIG. 3 shows the increase in measured concentration of total purines in arterial blood during carotid clamping. a) Plot of purine levels in the pre-operative phase (Pre), carotid clamp phase (Clamp) and after recovery (Post) for each patient. In every patient blood purine levels increase relative to the pre-operative baseline. Statistical comparison performed with the Friedman 2 way ANOVA. b) The same data plotted as cumulative probability distributions for the pre-operative, carotid clamp and recovery phases. Note that purine levels return to pre-operative levels in the recovery phase. Statistical comparison of medians performed with the Mann Whitney U test. A Kolmogorov Smirnov comparison of the cumulative probabilities of the pre-operative and clamp purine levels gives D=0.6667, with p=0.000.

Referring to FIG. 3, the effect of clamping of the carotid artery during a carotid endarterectomy procedure on awake patients is shown. This simulates the loss of blood flow to the brain in ischaemic stroke. Overall, the median resting purine level in blood, measured pre-operatively, was 2.4 µM (95% confidence interval 1.3 to 4.0 µM). During carotid clamping, the blood purine levels rose in every patient relative to the pre-operative baseline (FIG. 3a). This increase was equally apparent when the data for the blood levels in the pre-operative, clamp and recovery periods were plotted as cumulative probability distributions (i.e. treating the three conditions as independent samples, FIG. 3b). The median purine level in the clamp phase was 6.7 µM (4.7 to 11.5 µM). Following recovery the blood purines fell to the pre-operative baseline (1.9 µM, 1.4 to 2.7 µM). Our analysis shows that within a relatively short period following release of the clamp (less than 2 h) the blood purine levels are indistinguishable from the pre-operative baseline.

The results in FIG. 3 show that a threshold in the range 5 µM to 15 µM will indicate loss of cerebral blood flow, hence indicating stroke. The threshold value may be selected within that range to provide a chosen balance between false positive and false negative results. Referring to FIG. 3b for example, a threshold of 5 µM would place 13 subjects in the category that stroke is likely to be present, and 5 subjects in the category that ischaemia is present, as their purine levels are above the normal range of 1-2 µM, but that stroke is not detected by the method. Typically other diagnostic techniques would be used in such cases to exclude stroke. A threshold of 5 µM would include 4 subjects in the pre-operative phase. These subjects may be suffering from on-going occult chronic ischaemia, as discussed further in the example below, and so would merit clinical investigation, though would not be classified using this method alone as suffering from stroke. A threshold value of 8 µM would exclude all pre-operative results, and indicate stroke in 9 of 18 subjects. Additionally, patients of Types 1 and 2 (see discussion on patient types in the example) are indicated by the data to have effective compensation for loss of blood flow through carotid clamping through the Circle of Willis, and so the rise in purine levels in these patients in carotid clamping is likely to be less than that which would be observed in stroke, as in the case of stroke there is complete loss of blood flow to an area of the brain. Threshold values of 8 µM and above may be clinically relevant in diagnosis of stroke soon after the event. Threshold values of greater than 8 µM may be used in some embodiments, for example for use of the method with specific subpopulations of subjects, in order to detect serious, acute stroke shortly after the event, and to exclude false positive results from chronic ischaemic conditions, such as cardiac disease or critical limb ischaemia.

Figure 4:
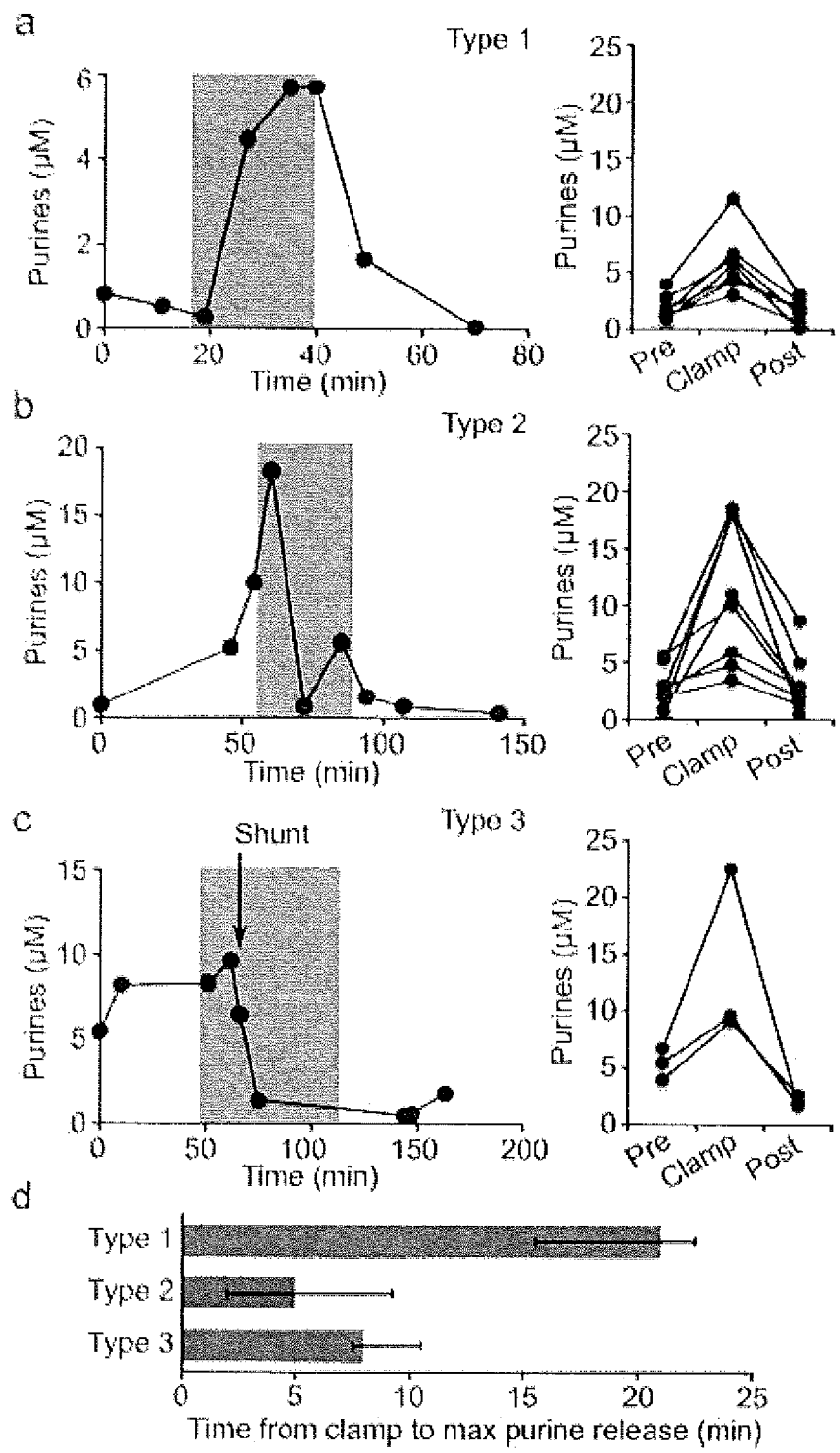
FIG. 4 shows sequential blood purine measurements during carotid endarterectomy for a number of awake patients, revealing different profiles of purine release. a) Left, an example of sequential measurements of blood purine levels in a Type 1 patient. The shaded rectangle indicates the timing and duration of the carotid clamping. Right, plots of the pre-operative, carotid clamp and recovery levels of purines for all Type 1 patients. b) Left, an example of sequential measurements of blood purine levels in a Type 2 patient. Right, plots of the pre-operative, carotid clamp and recovery levels of purines for all Type 2 patients. c) Left, an example of sequential measurements of blood purine levels in a Type 3 patient. Right, plots of the pre-operative, carotid clamp and recovery levels of purines for all Type 3 patients. d) Histograms of the median time from carotid clamp to maximal recorded purine release during the clamp phase for Type 1, 2 and 3 patients.

Referring to FIG. 4a-b (left) the method and device of the invention provides a means of monitoring the efficacy of a medical intervention in restoring cerebral blood flow. In patients of Types 1 and 2 (discussed further in the example) carotid clamping produces a rapid rise in purine levels as the oxygen supply is reduced, and a fall after it is restored. Referring to FIG. 3c (left) in patients of Type 3, who lost consciousness after the clamp was closed, a carotid shunt produced recovery of consciousness and a fall in the measured purine level. The measurement therefore shows the effectiveness of an intervention to restore blood flow, modelled by removal of the carotid clamp or introduction of a carotid shunt.

The method according to the invention and according to this embodiment will now be illustrated by the following non-limiting example.

Example 1 Carotid Clamping in Awake Carotid Endarterectomy

Microelectrode biosensors were used to measure the purine levels in untreated freshly drawn arterial blood from 18 consented patients undergoing awake carotid endarterectomy (CEA) under local anaesthetic. Samples were measured preoperatively, on exposure of the carotid artery, during the clamp phase, and during the recovery phase following removal of the clamp. The neurological status of each patient was recorded during the procedure.

Surgical Procedures

All CEAs were performed under loco-regional anaesthesia. The procedures were carried out using 3.5 time magnification and a selective shunt and patch policy was used. Before clamping of the carotids intravenous heparin was administered, using a fixed dose of 4000 units. Post operatively the patients were recovered overnight in a PACU (post anaesthetic care unit). Transcranial Doppler was used to assess post-operative cerebral micro-embolisation (Saedon M, et al. Registry report on kinetics of rescue antiplatelet treatment to abolish cerebral microemboli after carotid endarterectomy, Stroke 2013; 44(1): 230-3.14).

Neurological Assessment

Shunting was determined by awake-testing, the indication for shunting being profound neurological obtundation, or significant confusion, restlessness, or inability to respond to commands as determined by continuous clinical assessment by the anaesthetist. Profound deteriorations that occurred within the first 90 s were handled by declamping the artery and allowing the deficit to recover. The operation was then continued under general anaesthesia so that the carotid shunt could be inserted in a controlled fashion. A deficit that occurred more than 90 s after cross-clamp, but before the carotid arteriotomy (trial clamp for 5 minutes), was handled by temporary clamp release. Once normal neurology was restored, clamps were then reapplied allowing a shunt to be inserted before the patient became obtunded a second time (Imray C H et al. Oxygen administration can reverse neurological deficit following carotid cross-clamping. Br J Anaesth 2005; 95(2): 274; author reply 5).

Blood Sampling

An arterial line was inserted under local anaesthetic into the contralateral radial artery as part of the routine intra- and post-operative monitoring. Blood samples were drawn from this line in the anaesthetic room prior to surgery, during the exposure phase, prior to cross clamping, during the cross clamp phase, post clamp release, during closure and in the PACU.

Biosensor Measurements

Microelectrode biosensors as described in Tian F, Llaudet E, Dale N. Ruthenium purple-mediated microelectrode biosensors based on sol-gel film. Anal Chem 2007; 79(17): 6760-6, were used to measure the purines in fresh unprocessed blood. In brief these gold electrodes are coated with a Ruthenium Purple layer, which acts as a mediator to provide the necessary selectivity against interferences such as ascorbate, urate and acetaminophen. This allows the accurate measurement of purines in whole blood.

The purine sensor has an enzymatic layer containing a cascade of three enzymes as shown in FIG. 1 and referred to above as type (4), which allows it to detect all of the substrates for these enzymes: adenosine, inosine, hypoxanthine and xanthine (Tian F. et al. 2007 op. cit.; Llaudet E, Botting N P, Crayston J A, Dale N. A three-enzyme microelectrode sensor for detecting purine release from central nervous system. Biosens Bioelectron 2003; 18(1): 43-52). Amperometric measurements were made to detect the electroreduction of peroxide produced by the final enzyme in the detection cascade, xanthine oxidase. A "null" biosensor recording was used as a control comparison for each experiment. The null biosensors were identical to the purine biosensors in all respects except that they lacked the enzymatic cascade and therefore could not respond to the purines (Frenguelli B G, Llaudet E, Dale N. High-resolution real-time recording with microelectrode biosensors reveals novel aspects of adenosine release during hypoxia in rat hippocampal slices. J Neurochem 2003; 86(6): 1506-15).

Figure 2:
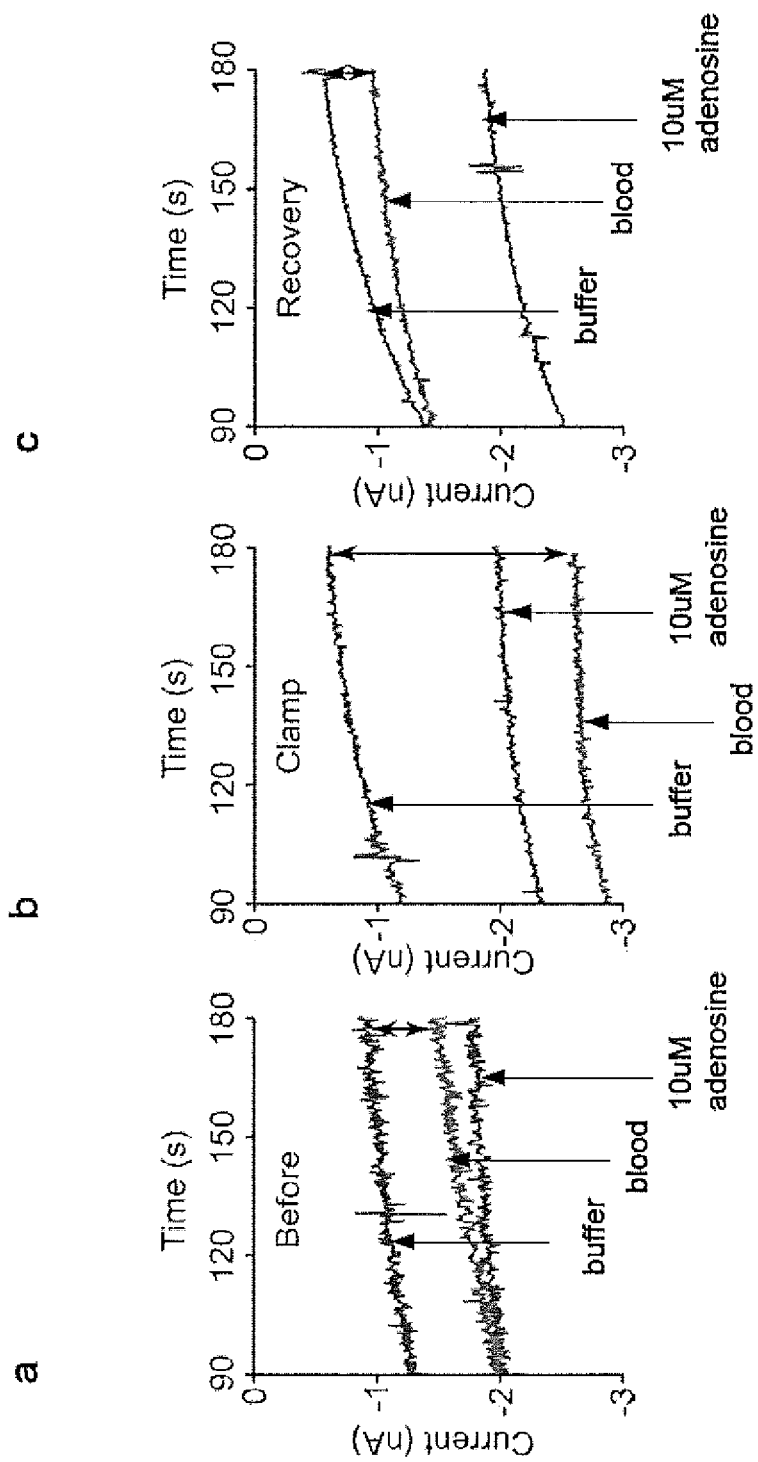
FIG. 2 shows example records of sensor currents during blood measurements from a type 3 patient as discussed in the examples, showing the pre-operative blood purine level, shortly after carotid clamping, and following recovery.

FIG. 2 shows example records of sensor currents during blood measurements from a type 3 patient made (a) pre-operatively, (b) shortly after carotid clamping, and (c) following recovery. The biosensors were polarized to −50 mV with respect to a Ag/AgCl pseudo-reference electrode for 180 s. The current records show the last 90 s of the measurement and are the difference between the purine and null biosensors. The traces show a "zero current" in buffer, calibration with 10 µM adenosine, and measurement in whole blood. The purine concentration in blood is calculated by taking the difference between the blood and buffer traces (black double headed arrows), and expressing this as a proportion of the difference between the calibration and buffer traces.

Both the null and purine biosensors were introduced into the blood sample as soon as possible after sampling. They were simultaneously polarized to the working potential of −50 mV (versus Ag/AgCl), and the amperometric faradaic charging currents recorded as shown in FIG. 2. After 3 minutes the current value of the null sensor was subtracted from the purine biosensor to give the "purine current". This was converted into a purine concentration by comparing it to the current obtained from calibrating the sensors in a known amount of adenosine.

Statistical Presentation and Analysis

All data are presented as medians with 95% confidence limits. In the case of the smaller subgroups of the data (Type 1, 2 and 3 patients) the 95% confidence limits are the same as the range of the data. For the entire group the data was analyzed in a 2 way Friedman ANOVA comparing the pre-clamp, clamp and recovery phase purine levels within each patient, the medians and distributions being compared via the Mann Whitney U test and the Kolmogorov Smirnov tests respectively.

Results

Measurements were collected from 18 patients. First the data obtained from these patients was analysed as a single group. Overall, the median resting purine level in blood, measured pre-operatively, was 2.4 µM (1.3 to 4.0 µM). This value is comparable to others in the literature which suggest that plasma concentrations of hypoxanthine/xanthine (the predominant purines in blood) in humans to be in the range 1-2 µM (Yamamoto T et al. Effect of ethanol and fructose on plasma uridine and purine bases. Metabolism 1997; 46(5): 544-7; Ohno M, et al. Effects of exercise and grape juice ingestion in combination on plasma concentrations of purine bases and uridine. Clin Chim Acta 2008; 388(1-2): 167-72). During the carotid clamping, the blood purine levels rose in every patient relative to the pre-operative baseline. The median purine level in the clamp phase was 6.7 µM (4.7 to 11.5 µM). Following recovery the blood purines fell to the pre-operative baseline (1.9 µM, 1.4 to 2.7 µM). The analysis shows that for the group of patients as a whole within a relatively short period following release of the clamp (less than 2 hours (h)) the blood purine levels are indistinguishable from the pre-operative baseline.

Inspection of the profile of repeated sequential measurements of blood purines made throughout the carotid procedure, combined with the concomitant neurological assessment of the patients, enabled the cohort to be divided into three groups: Type 1, Type 2 and Type 3. Type 1 and 2 patients (7/18 and 8/18 respectively), displayed no major neurological symptoms during carotid clamping. However Type 3 patients (3/18) rapidly became unconscious following the clamping of the carotid artery.

Results are described with reference to FIG. 3, which shows a) Left, an example of sequential measurements of blood purine levels in a Type 1 patient. The shaded rectangle indicates the timing and duration of the carotid clamping. Right, plots of the pre-operative, carotid clamp and recovery levels of purines for all Type 1 patients. b) Left, an example of sequential measurements of blood purine levels in a Type 2 patient. Right, plots of the pre-operative, carotid clamp and recovery levels of purines for all Type 2 patients. c) Left, an example of sequential measurements of blood purine levels in a Type 3 patient. The patient lost consciousness shortly after application of the carotid clamp, necessitating rapid installation of a carotid shunt (arrow) to restore cerebral blood flow. Note how purine levels rapidly dropped following installation of the shunt. Right, plots of the pre-operative, carotid clamp and recovery levels of purines for all Type 3 patients. d) Histograms of the median time from carotid clamp to maximal recorded purine release during the clamp phase for Type 1, 2 and 3 patients. Error bars are upper and lower quartiles.

In Type 1 patients, the rise in purine levels was sustained throughout the clamp period and reached its maximum towards the end of the clamp period (FIG. 3a). In these patients the median time to maximal purine blood level was 21 minutes (14 to 29 minutes, FIG. 3d). For Type 1 patients the median preoperative purine level was 1.5 µM (0.8 to 4.0

μM). During carotid clamping it rose to 5.7 μM (3 to 11.5 μM) and during the recovery period it fell to 1.8 μM (0.05 to 3.1 μM, FIG. 3a).

Type 2 patients had preoperative baseline purines of 2.4 μM (0.7 to 5.6 μM), and they exhibited a transient pattern of purine release during the carotid clamping. Their blood purines reached a peak (10.0 μM, range 3.4 to 18.6 μM) much quicker than Type 1 patients (3 minutes, 1 to 16 minutes, p=0.001, Mann Whitney U test compared to Type 1 patients, FIGS. 3b, 3d). After reaching this peak, the blood purine levels declined, but in 6/8 cases remained higher than the pre-operative baseline (3.2 μM, 0.9 to 13.6 μM). On recovery the purine levels returned to 2.2 μM (0.4 to 8.7 μM, FIG. 3b)

Type 3 patients (n=3) rapidly became unconscious following carotid clamping. The baseline purine levels were elevated compared to the Type 1 and Type 2 patients (5.4 μM, 3.9 to 6.7 μM, FIGS. 3c, 3d). The purines rose on clamping to 9.6 μM (9.1 to 22.5 μM), before falling to 1.8 μM (1.8 to 2.6 μM) during recovery following the procedure. This recovery value was lower than the preoperative baseline value. Importantly, when the carotid artery was shunted to restore cerebral blood flow, the blood purine levels dropped to below the pre-operative baseline levels (1.4 μM, 0.4 to 2.9 μM). This observation suggests that the brains of these patients are chronically ischaemic owing to impeded carotid blood flow, which was relieved by the shunt (hence the purine levels fell), and also in the longer term by the outcome of the operation.

Discussion

CEA is performed to reduce the risk of a future stroke. As the timing and release of the carotid clamp and hence the ischemic insult is defined, this procedure provides an excellent opportunity to test in human patients whether purine levels in blood are a marker of cerebral ischaemia. In all 18 patients purine levels in arterial blood rose within minutes of applying the carotid clamp. In most patients this occurred in the absence of any major neurological indication. This shows that the purines are a very sensitive measure of cerebral ischaemia. Elevated purine levels were observed throughout the clamp period, demonstrating that the purines are continually produced and released from brain while the ischaemic insult persists. Following release of the clamp, the blood purine levels returned relatively quickly (within 1-2 hours) to the pre-clamp baseline. The purines are thus a relatively short lasting indication of cerebral ischaemia. This implies that the purines could be used firstly, to detect incidence of cerebral ischaemia from its earliest origins and secondly, to monitor the persistence of the ischaemic insult.

The patients in these examples were separated into 3 groups based on their purine release profiles during the procedure, and whether they lost consciousness. Type 1 patients, because they exhibit a rather slower increase in blood purines, may retain a higher ability than either of the other two patient groups to compensate for the loss of blood flow from the ipsilateral carotid artery by enhancing flow from the contralateral side via the Circle of Willis. In type 1 patients, the compensatory flow has a rapid onset coincident with the restriction of blood flow on the ipsilateral side, and this has the effect of slowing and limiting the purine rise during carotid clamping.

The results suggest that type 2 patients may retain some ability for contralateral compensation but that the onset of the compensation is delayed—hence the tendency to higher initial increases in blood purines, and the later fall of purine levels during the clamp phase.

Type 3 patients rapidly lost consciousness during carotid clamping. The results suggest that they have lost the ability to compensate with enhanced blood flow from the contralateral side. Furthermore as their blood purines were high even at the pre-operative stage, their brains may be under chronic ischaemic stress.

The example shows that for all patients carotid clamping, which models ischaemic stroke, resulted in a rapid rise in purine concentration in the arterial blood as measured using methods and with biosensors described herein, and that a measured concentration greater than a threshold concentration in the range 5 μM to 15 μM could be used to indicate loss of cerebral blood flow, and hence stroke.

The example also shows that a change in a measured concentration over time may show a change in the degree of acute ischaemic disorder in a patient, such as an increase in the severity of acute ischaemic disorder as in the case of carotid arterial clamping (for example as shown by the rise in the purine level during clamping in FIG. 4a (left), and a reduction in the degree of acute ischaemic disorder following restoration of cerebral blood flow following removal of the carotid clamp (FIG. 4b (left)) or introduction of a carotid shunt (FIG. 4c (left)).

Example 2 Measurements of Purines in Stroke Patients

Total purine concentration as described above was measured in samples of peripheral blood of patients admitted with suspected stroke. Control measurements were made in samples from relatives of the patients, not suspected to have ischaemic disease.

Biosensor Array

A device configured to inter-fit with a Vacutainer™ sampling device as disclosed in pending international patent application WO2014087137, referred to herein as a 'SMARTCap' array of microelectrode biosensors, was used to make measurements of purines from samples of fresh blood drawn using the Vacutainer. Each SMARTCap array had 4 working electrodes and 2 Ag/AgCl pseudoreference electrodes. The working electrodes were gold electrodes, coated with a Ruthenium Purple layer which acts as a mediator to provide the necessary selectivity against interferences such as ascorbate, urate and acetaminophen (Tian F, Llaudet E, Dale N (2007) Anal Chem 79:6760-6766). Two of the working electrodes had an additional gel layer containing a cascade of three enzymes (adenosine deaminase, nucleoside purine phosphorylase and xanthine oxidase), to allow detection of all of the substrates for the three enzymes: adenosine, inosine, hypoxanthine and xanthine (Llaudet E, Botting N P, Crayston J A, Dale N (2003) Biosens Bioelectron 18:43-52, Tian et al., 2007). In the other two working electrodes, "null sensors", the additional gel layer that lacked the enzymes but in all other respects the null sensors were identical to the purine biosensors. Lacking the necessary enzymes, the null sensors could not respond to the purines and therefore acted as a control for the purine biosensor measurements and to establish the zero current level for the electrochemical measurements (Tian et al., 2007). The SMARTCap array was used in an chronoamperometric measuring mode to detect the electroreduction of peroxide produced by the final enzyme in the detection cascade, xanthine oxidase.

Recruitment of Patients

Suspected stroke patients were recruited to the study if they were FAST-positive (Face Arm Speech Test) at the time of admission to the Emergency Department and were within 4.5 hours of onset of symptoms. The healthy controls were the relatives of the stroke patients and who displayed no obvious signs of, and had no history of, vascular disease.

Measurement in Blood

A SMARTCap biosensory array was prepared by hydrating it in a phosphate buffered saline (PBS), pH 7.4, and calibrating against a known amount of adenosine in PBS. Blood was collected from the patient or healthy control in a EDTA-containing vacutainer. The calibrated SMARTCap biosensor array was introduced into the blood sample as soon as possible after sampling (within minutes). The 4 working electrodes of the SMARTCap were simultaneously polarized to the working potential of −50 mV (versus Ag/AgCl), and the amperometric faradaic charging currents recorded for 3 minutes. After 3 minutes the current value of the null sensor was subtracted from the purine biosensor to give the "purine current". This was converted into a purine concentration by comparing it to the current obtained during the prior calibration step.

Results

Figure 5:
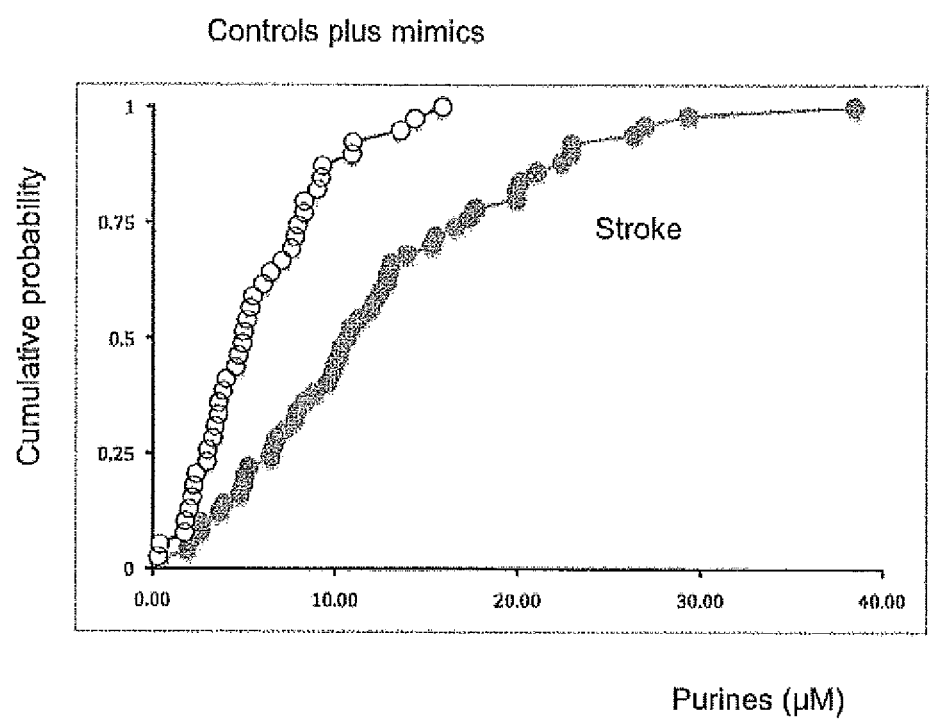
FIG. 5 shows concentrations of total purines in samples of peripheral venous blood from patients admitted with suspected stroke and healthy controls, plotted as cumulative probability distributions. Patients initially suspected of stroke but later found not to have a stroke ('mimics') are included with the controls.

Referring to FIG. 5, the distribution of measured total purine concentrations from the stroke patients is highly significantly different from that from the controls plus mimics (stroke: median 10.8 μM, 95% confidence limits 8.4 to 13.1 μM, N=50; controls plus mimics: median 5.0 μM, 95% confidence limits 3.6 to 7.6 μM, N=39; Mann-Whitney U test U=447, p=0). Mimics included conditions not finally diagnosed as stroke and are included in the control group. It can be seen that the threshold of 5 μM will exclude 50% of the controls plus mimics, and around 20% of the stroke patients. A threshold of 15 μM will exclude substantially all of the controls plus mimics and around 67% of the stroke patients. A threshold may be chosen between these values to balance false positive and false negative results, and a different threshold may be chosen for specific subpopulations of patients. For example, a threshold near the lower end of the range, for example 5-8 μM, may be too low for the patient population as a whole, but may be useful for a younger, fitter population for example, and similarly a threshold near the upper end of the range, for example 12-15 μM, may be useful for an older population, or one that has a history of a chronic ischaemic condition and a high baseline purine level, and for whom a rise above the baseline may indicate a worsening of the condition or acute disorder. It can be seen that a threshold may be selected, based on data shown in FIG. 5 so as to select the ratio of false positive to false negative results that may result from the method or from use of a device to carry it out. Such a threshold may be one of the values listed herein, such as 5.0, 6.0, 7.0, 8.0, 9.0, 10.0, 11.0, 12.0, 13.0, 14.0 or 15.0 μM or a value lying between two of those values.

The method of the invention comprises collecting data comprising measurement of purines in the body fluid of stroke patients and of controls and using the data to determine a threshold for use in the method. For example, the method may comprise deriving cumulative probability distributions for the test and control groups, and using the cumulative probability distributions to select the threshold. The method may comprise collecting further data and modifying the selected threshold in the light of the further data, for example for the overall population of stroke patients, and may comprise allocating patients to one or more subpopulations and using data from the said subpopulation to derive a threshold for the subpopulation.

Figure 7:
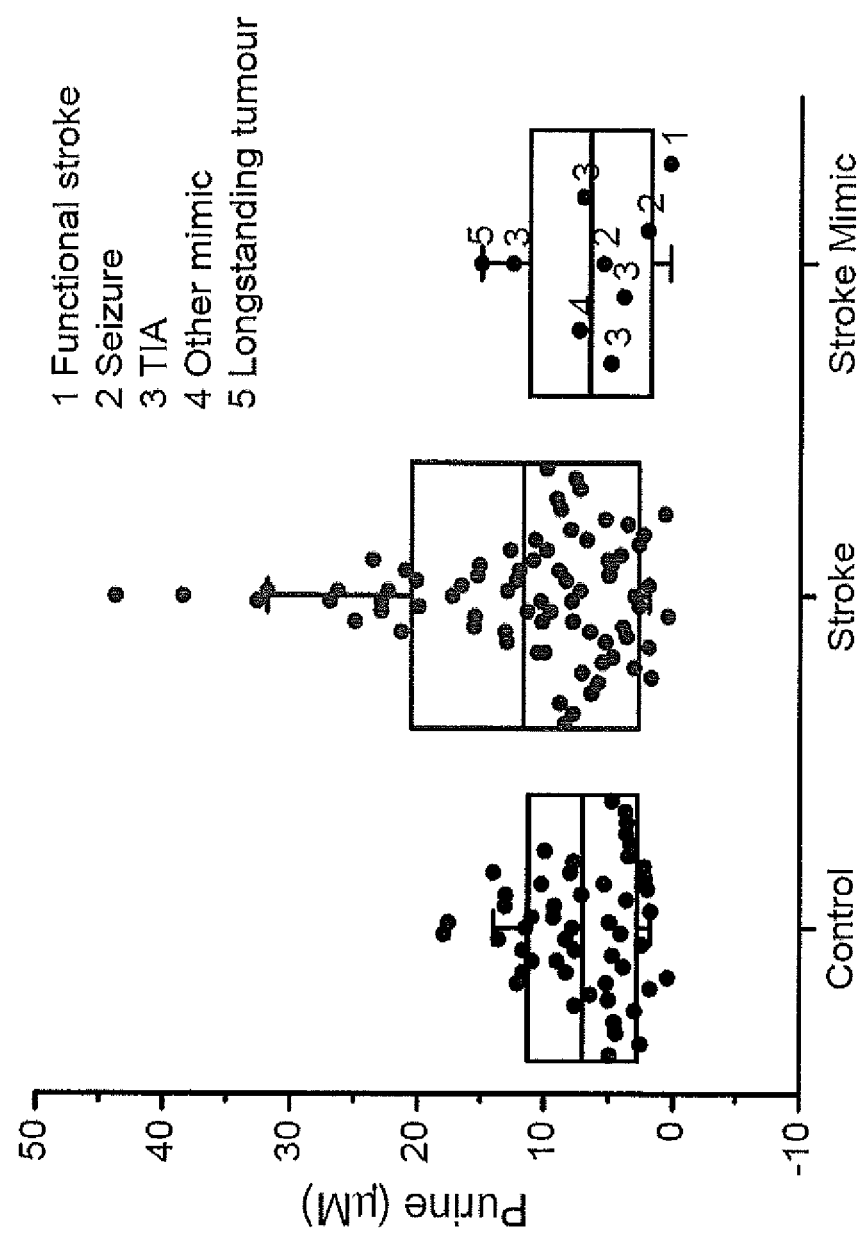
FIG. 7 shows that lower concentrations of purine may be used to distinguish ischaemia from stroke mimics, including (1) functional stroke, (2) seizure, (3) transient ischaemic attack, (4) other mimic, (5) long standing tumour.

As FIG. 7 shows, the concentration of purine may be used to identify stroke mimics to exclude that a patient has cerebral ischaemia.

The invention has been described by way of examples only and it will be appreciated that variation may be made to the above-mentioned embodiments without departing from the scope of invention.

With respect to the above description then, it is to be realised that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A method of determining the presence of an acute cerebral ischaemic disorder in a subject, the method comprising:
   a. measuring the concentration of one or more purines in a body fluid of the subject using a biosensor comprising an electrochemical cell, where the purines are selected from the group consisting of adenosine, inosine, hypoxanthine, xanthine, and ATP, and
   b. comparing the measured concentration with a threshold concentration of the one or more purines, wherein the threshold concentration is in the range from about 5 μM to about 15 μM and wherein a measured concentration higher than the threshold concentration indicates the presence of the acute cerebral ischaemic disorder.

2. The method of claim 1 wherein the acute ischaemic disorder is a stroke, a traumatic head injury, or a transient ischaemic attack (TIA), or a combination thereof.

3. The method of claim 1 wherein the threshold concentration is in the range from about 5 μM to about 10 μM.

4. The method of claim 1 wherein the threshold concentration is in the range from about 8 μM to about 15 μM.

5. The method of claim 1 wherein the measured concentration is the total of the concentrations of two or more single purines each measured individually.

6. The method of claim 5 wherein one of the purines is adenosine, xanthine, inosine, or ATP, and the threshold concentration is in the range from about 5 μM to about 10 μM; or one of the purines is hypoxanthine, and the threshold concentration is in the range from about 5 μM to about 15 μM.

7. The method of claim 1 wherein the measured concentration is an equivalent total purine concentration measured by a measurement method responsive to two or more of said purines, and the total purine measurement is calibrated relative to the response of the method to a single calibration purine.

8. The method of claim 7 wherein the calibration purine is adenosine.

9. The method of claim 1 wherein the threshold concentration is 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5 or 15.0 μM.

10. The method of claim 1 wherein the body fluid is whole blood.

11. The method of claim 1 wherein the purine concentration is measured using a biosensor comprising an electrode having immobilized on the electrode one or more enzymes for which at least one of the said purines is a substrate, and a ruthenium purple mediator.

12. A device configured to carry out the method of claim 1, wherein the acute ischaemic disorder is a stroke, a traumatic brain injury, or a transient ischaemic attack (TIA), or a combination thereof, the device comprising a biosensor adapted to measure the concentration of one or more purines in a body fluid, where the purines are selected from the group consisting of adenosine, inosine, hypoxanthine, xanthine, and ATP.

13. The device of claim 12 wherein the biosensor comprises an enzyme electrode having immobilized on it an enzyme for which at least one of the said purines is a substrate, and a ruthenium purple mediator.

14. The device of claim 12 wherein the biosensor comprises an enzyme sensor responsive to all four of adenosine, inosine, hypoxanthine, and xanthine.

15. The device of claim 12 further comprising a controller configured to measure signals from the biosensor and configured to:
    measure a reference signal at a first elapsed time after the biosensor is contacted with a reference liquid,
    measure a measurement signal at a second elapsed time, optionally substantially the same as the first time, after the biosensor is contacted with a body fluid, and
    derive the measured concentration of the one or more purines from the said signals.

16. The device of claim 15 wherein the controller is configured to:
    measure a calibration signal at a third elapsed time, optionally substantially the same as the first or the second elapsed time, after the biosensor is contacted with a calibration liquid, and
    compare the measurement signal with the calibration signal to derive the measured concentration of the one or more purines.

17. The device of claim 15 wherein the said first elapsed time is within the range of 5 seconds to 600 seconds.

18. The device of claim 12 further comprising a test chamber, where the biosensor is within the test chamber, and wherein the device is configured to introduce a reference liquid or a calibration liquid into the test chamber and to introduce the sample into the test chamber under control of the controller.

19. A method of determining the absence of an acute cerebral disorder in a subject comprising:
    a. measuring the concentration of one or more purines in a body fluid of the subject using a biosensor comprising an electrochemical cell, where the purines are selected from the group consisting of adenosine, inosine, hypoxanthine, xanthine, and ATP, and
    b. comparing the measured concentration with a threshold concentration of the one or more purines, wherein the threshold concentration is below about 4 µM and wherein a measured concentration lower than the threshold concentration indicates the absence of an acute cerebral ischaemic disorder.

20. A method of determining the presence of an acute cerebral ischaemic disorder in a subject, the method comprising:
    measuring the concentration of one or more purines in a body fluid of a subject using a biosensor comprising an electrochemical cell at two or more time points, where the purines are selected from the group consisting of adenosine, inosine, hypoxanthine, xanthine, and ATP, and
    deriving the rate of change of the measured concentration, and
    comparing the rate of change with a threshold value for the rate of change, where a rate of change above the threshold rate of change indicates that the acute ischaemic disorder is present.

21. A method of determining the presence of an acute cerebral ischaemic disorder in a subject, the method comprising:
    measuring the concentration of one or more purines in a body fluid of the subject using a biosensor comprising an electrochemical cell, where the purines are selected from the group consisting of adenosine, inosine, hypoxanthine, xanthine, and ATP, and
    measuring the rate of change of the concentration of one or more of said purines, and
    using the measured concentration and the measured rate of change to determine the presence of the acute ischaemic disorder in the subject.

22. The method of claim 20 wherein the rate of change threshold is in the range from about 2 µM to about 8 µM per hour.

* * * * *